US012691239B2

(12) United States Patent
Yu et al.

(10) Patent No.: US 12,691,239 B2
(45) Date of Patent: Jul. 28, 2026

(54) RESPIRATORY OR SURGICAL HUMIDIFIER AND METHOD OF USE

(71) Applicant: Fisher & Paykel Healthcare Limited, Auckland (NZ)

(72) Inventors: Yintao Yu, Auckland (NZ); Sinaa Alnashi, Auckland (NZ); Wenjie Robin Liang, Auckland (NZ); Jonathan Luke Hoi-Man Tsang, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 889 days.

(21) Appl. No.: 17/759,975

(22) PCT Filed: Feb. 3, 2021

(86) PCT No.: PCT/NZ2021/050013
§ 371 (c)(1),
(2) Date: Aug. 2, 2022

(87) PCT Pub. No.: WO2021/158127
PCT Pub. Date: Aug. 12, 2021

(65) Prior Publication Data
US 2023/0065301 A1 Mar. 2, 2023

Related U.S. Application Data

(60) Provisional application No. 62/970,047, filed on Feb. 4, 2020.

(51) Int. Cl.
*A61M 16/00* (2006.01)
*A61M 16/10* (2006.01)
*G16H 40/63* (2018.01)

(52) U.S. Cl.
CPC ........ *A61M 16/024* (2017.08); *A61M 16/109* (2014.02); *G16H 40/63* (2018.01);
(Continued)

(58) Field of Classification Search
None
See application file for complete search history.

(56) References Cited

U.S. PATENT DOCUMENTS

| | | | |
|---|---|---|---|
| 4,300,063 A | 11/1981 | Dunphy et al. | |
| 4,324,990 A | 4/1982 | Gay | |

(Continued)

FOREIGN PATENT DOCUMENTS

| | | | |
|---|---|---|---|
| DE | 2427326 B1 | 12/1975 | |
| EP | 2775277 B1 | 5/2017 | |

(Continued)

OTHER PUBLICATIONS

International Search Report in corresponding International Patent Application No. PCT/NZ2021/050013, dated May 7, 2021, in 6 pages.

(Continued)

*Primary Examiner* — Timothy A Stanis
*Assistant Examiner* — Thomas Z Chang
(74) *Attorney, Agent, or Firm* — Knobbe, Martens, Olson & Bear, LLP

(57) ABSTRACT

An improved system and method of monitoring the operation of a respiratory or surgical humidifier system. A controllable load can be connected across output terminals to a tube heating element to test the operation of a tube heating element supply circuit. A range of tests may be performed by controlling the state of one or more components and monitoring one or more sensors. Tests may be performed either during or not during therapy and either with a gas supply tube connected or not. Transient currents may also be detected and the power supply to a tube heating element can be stopped where transient currents outside a permitted range are detected.

17 Claims, 5 Drawing Sheets

Figure 2

(52) U.S. Cl.
CPC ............... *A61M 2205/3317* (2013.01); *A61M 2205/3327* (2013.01); *A61M 2205/3653* (2013.01); *A61M 2205/702* (2013.01)

(56) References Cited

U.S. PATENT DOCUMENTS

| | | | | |
|---|---|---|---|---|
| 4,489,285 | A | 12/1984 | Sato | |
| 4,926,281 | A * | 5/1990 | Murphy | H01H 47/002 |
| | | | | 324/415 |
| 5,237,991 | A * | 8/1993 | Baker, Jr. | A61N 1/372 |
| | | | | 607/27 |
| 5,357,186 | A | 10/1994 | Pennisi et al. | |
| 6,556,050 | B2 | 4/2003 | Therisod | |
| 6,598,604 | B1 * | 7/2003 | Seakins | H02H 1/0015 |
| | | | | 219/481 |
| 6,605,965 | B1 | 8/2003 | Fernandez-Texon | |
| 6,948,503 | B2 * | 9/2005 | Refior | A61B 18/1206 |
| | | | | 606/34 |
| 7,061,252 | B2 * | 6/2006 | Bouton | A61M 16/1095 |
| | | | | 219/67 |
| 7,140,367 | B2 | 11/2006 | White et al. | |
| 7,306,205 | B2 | 12/2007 | Huddart et al. | |
| 7,725,182 | B2 | 5/2010 | Sutardja | |
| 7,728,633 | B2 | 6/2010 | Moindron | |
| 7,983,542 | B2 | 7/2011 | McGhin et al. | |
| 8,063,343 | B2 | 11/2011 | McChin et al. | |
| 8,416,546 | B2 | 4/2013 | Arndt et al. | |
| 9,222,966 | B2 | 12/2015 | Amanuma | |
| 9,952,286 | B2 | 4/2018 | Kato | |
| 10,524,312 | B2 * | 12/2019 | Knappenberger | H02H 3/167 |
| 10,779,876 | B2 | 9/2020 | Monson et al. | |
| 10,960,167 | B2 * | 3/2021 | Liu | A61M 16/161 |
| 2007/0046263 | A1 * | 3/2007 | Matsushima | H02J 7/005 |
| | | | | 320/132 |
| 2012/0249038 | A1 * | 10/2012 | Wei | G01R 31/52 |
| | | | | 318/490 |
| 2013/0229192 | A1 * | 9/2013 | Behringer | G01R 11/02 |
| | | | | 324/658 |
| 2014/0216459 | A1 * | 8/2014 | Vos | A61M 16/16 |
| | | | | 128/204.17 |
| 2018/0028773 | A1 | 2/2018 | Klasek et al. | |
| 2019/0001091 | A1 | 1/2019 | Bath et al. | |
| 2021/0008312 | A1 * | 1/2021 | Young | G06F 21/6245 |
| 2021/0288515 | A1 * | 9/2021 | Conrad | H02J 7/0047 |

FOREIGN PATENT DOCUMENTS

| | | | |
|---|---|---|---|
| EP | 2770932 | B1 | 12/2018 |
| GB | 2159286 | A | 11/1985 |
| WO | WO 01/13981 | A1 | 3/2001 |
| WO | WO 2017/043981 | A1 | 3/2017 |
| WO | WO 2021/158127 | A1 | 8/2021 |

OTHER PUBLICATIONS

Written Opinion in corresponding International Patent Application No. PCT/NZ2021/050013, dated May 7, 2021, in 6 pages.
International Preliminary Report on Patentability in corresponding International Patent Application No. PCT/NZ2021/050013, dated Jul. 28, 2022, in 7 pages.

* cited by examiner

RESPIRATORY OR SURGICAL HUMIDIFIER AND METHOD OF USE

INCORPORATION BY REFERENCE TO ANY PRIORITY APPLICATIONS

Any and all applications for which a foreign or domestic priority claim is identified in the Application Data Sheet as filed with the present application, namely PCT/NZ2021/050013 and U.S. Provisional Application 62/970,047, are hereby incorporated by reference under 37 CFR 1.57.

FIELD OF THE DISCLOSURE

The present disclosure relates to respiratory and/or surgical humidifiers, and respiratory or breathing assistance systems for gases to be supplied to a patient or user via a gas supply tube incorporating a tube heating element.

BACKGROUND OF THE INVENTION

Respiratory and/or surgical humidifiers are used in various environments, such as hospital, medical facility, residential care, palliative care and home environments. For a range of respiratory applications, it is beneficial to humidify gases being supplied to a patient or user. These applications include where the gases are for breathing by the patient or user and where the gas is being supplied during surgery to the patient or user.

In the case of noninvasive ventilation therapy (e.g. with a face or nasal mask), inhalation of dry breathing gasses can dry out the tissues of the patient or user's airway (e.g., the nasal mucosa). Humidifying the breathing gasses prior to inspiration can mitigate drying of the patient or user's airway tissue. Furthermore, this humidification can increase the patient or user's comfort, and improve the patient or user's tolerance to the noninvasive ventilation (NIV).

In the case of high flow therapy, humidified gases are delivered to the patient or user at high flows through an unsealed interface. The patient or user may be spontaneously breathing or may be apneic, such as under anesthesia. As with noninvasive ventilation, humidifying the gases inspired during high flow therapy can mitigate drying of the airway tissue, increase comfort, and improve tolerance to the therapy.

In the case of positive airway pressure (PAP) therapy, a PAP apparatus (that includes a blower and a humidifier) can be used to provide pressure therapy to the patient or user. This therapy may be in the form of, for example, continuous positive airway pressure therapy (CPAP). As with noninvasive ventilation and high flow therapy, humidifying the gases inspired during PAP therapy can mitigate drying, increase comfort, and improve tolerance.

In the case of surgical gases, or invasive ventilation (when the gases delivered to the patient bypass the upper airway), humidification of the gases has been found to improve patient comfort and provide physiological benefits (such as improved mucus transport). Furthermore, humidification can be necessary for improving post-operative outcomes, and for ensuring patient or user safety. For example, humidification can help to prevent airway obstruction (caused by inspissation of airway secretion) and/or disruption of the airway epithelium.

In any of the therapies mentioned above, humidified gases can be delivered to a patient via a gas supply tube. This tube can be heated by an in-built tube heating element. Heating the gas supply tube prevents condensation of the warm, humid breathing gases as they travel from the humidifier to the patient. Preventing this condensation helps to ensure that the breathing gases are supplied to the patient or user at the required temperature and humidity.

SUMMARY

If a humidifier malfunctions during use, then the gases supplied to the patient (via the gas supply tube) may not be correctly humidified. Incorrect humidification can result in risks to the patient (or other user). These risks can include, for example, transient currents in the tube heating element, prolonged exposure of the airway to dry gases, discomfort, condensation blocking the airflow, high enthalpy being conveyed to the patient, high surface temperature of the gas supply tube or damage to the respiratory humidifier system.

For a humidifier to operate correctly, all of the subsystems within it must operate correctly. If a fault (capable of causing malfunction) occurs in any of these sub-systems, the humidifier must have means to identify the fault and alert the person administering the therapy (e.g. a healthcare professional or the patient themselves in the case of home-based administration). The present disclosure is focused on detecting faults associated with two humidifier sub-systems: the gas supply tube heating element and the power supply path—which transfers power from the heater base unit to the gas supply tube heating element.

Some existing humidifiers have systems that can detect fault conditions (in the gas supply tube heating element and the power supply path). However, these systems have limitations. For example, these fault-detection systems may be complex, may perform only a limited range of tests, may not allow detection of certain faults during therapy, and may only be capable of detecting faults when a gas supply tube with a heating element is connected.

The present disclosure provides examples of humidifier fault-detection systems that overcome some of the limitations in existing humidifier fault-detection systems—specifically those used to detect faults associated with the gas supply tube heating element and its power supply path. The fault-detection systems and methods in the present disclosure are based on monitoring power attributes when a switchable load is switched into the power supply path. This switching and monitoring may be performed regardless of whether there is a gas supply tube (with a functioning heating element) attached. This switching and monitoring may also be performed during therapy without any interruption to therapy. The fault-detection systems disclosed herein can also have any of the following advantages, and/or other advantages. For example, the monitoring systems and methods disclosed herein allow a wide range of tests to be performed using relatively simple additional components. Such tests may include detecting any of a number of possible fault conditions. These fault conditions may include a power flow controller fault (such as an open-circuit or short-circuit fault), a current sensor fault, a tube heating element fault, or a general fault. Such tests may also be used to detect the presence of a tube heating element. Furthermore, the implementation is simple, reliable, robust and inexpensive.

The detection and/or alarm methods described herein can be incorporated into a variety of respiratory and/or surgical humidifier systems, such as CPAP devices, high flow therapy devices, surgical humidifiers, respiratory humidifiers, infant CPAP devices, infant high flow devices, NIV therapy devices, and the like.

In some configurations, a respiratory or surgical humidifier can comprise power supply lines configured to supply power via a supply path to respective output terminals; a switchable load electrically connected across the output terminals; a control circuit configured to control switching of the switchable load; and a sensor that monitors at least one attribute of power supplied via the supply path and provides attribute information to the control circuit. The control circuit may be configured to control the switchable load to operate in different states and determine operation of the respiratory or surgical humidifier based on the attribute information for the different states.

In some configurations, the control circuit can be configured to control the switchable load to test the respiratory or surgical humidifier whilst power is supplied to a tube heating element electrically connected across the output terminals.

In some configurations, the respiratory or surgical humidifier can include a power flow controller controlled by the control circuit to vary the level of power supplied via the supply path.

In some configurations, the power flow controller can be a controllable switch in the supply path.

In some configurations, the control circuit can control state combinations of the switchable load and power flow controller to monitor operation of the respiratory or surgical humidifier based on the attribute information for the different state combinations.

In some configurations, the switchable load can include a controllable switch and an impedance.

In some configurations, the controllable switch can be a semiconductor switch.

In some configurations, the impedance can be a resistor.

In some configurations, the impedance can include a reactive impedance.

In some configurations, a voltage sensor can be provided across the power supply lines.

In some configurations, the attribute information can include the voltage across the power supply lines.

In some configurations, the sensor can be a current sensor.

In some configurations, the sensor can be an inductive, Hall effect, or shunt resistance-based sensor.

In some configurations, the attribute information includes the current flowing in the supply path.

In some configurations, the control circuit can be configured to switch the power flow controller on whilst the switchable load is switched off and receive current information from the current sensor representing a first current level.

In some configurations, the control circuit can be configured to detect an error if the first current level is outside a permitted range.

In some configurations, the control circuit can be configured to switch the power flow controller on whilst the switchable load is switched on and receive current information from the current sensor representing a second current level.

In some configurations, the control circuit can be configured to detect an error if the difference between the first and second current levels is outside a permitted range.

In some configurations, the control circuit can be configured to detect an error if the difference between the first current level and an expected first current level or the difference between the second current level and an expected second current level is outside a permitted range.

In some configurations, the expected first current level, expected second current level or the permitted range for the difference between the first and second current levels can be determined on the basis of a voltage level across the output terminals and a switchable load impedance and a tube heating element impedance.

In some configurations, the permitted current range can be a permitted current level plus or minus a margin of error.

In some configurations, the control circuit can be configured to detect a fault if neither the first or second current is above a minimum threshold level.

In some configurations, the control circuit can be configured to receive current information from the current sensor when the power flow controller is switched off and the switchable load is switched on, and detect a fault if the current is above a low current threshold level.

In some configurations, a transient current detector can be provided in the supply path.

In some configurations, the transient current detector can include a pair of transistors configured to detect positive or negative transient voltages across an inductor in the supply path.

In some configurations, a respiratory or surgical humidifier can comprise a power flow controller configured to control power supplied via a supply path to respective output terminals; a switchable load electrically connected across the output terminals; a current sensor that monitors current supplied via the supply path to develop current information; a control circuit configured to receive the current information from the current sensor, control the power flow controller to supply power via the output terminals, and control switching of the switchable load with the control circuit configured to: switch the power flow controller on whilst the switchable load is switched off and receive current information from the current sensor representing a first current level; switch the power flow controller on whilst the switchable load is switched on and receive current information from the current sensor representing a second current level; and determine operation of the respiratory humidifier based on at least the first and second current levels.

In some configurations, a respiratory or surgical humidifier can comprise power supply lines configured to supply power via a supply path to respective output terminals; a switchable load electrically connected across the output terminals; a current sensor that monitors current supplied via the supply path to develop current information; a control circuit configured to receive the current information from the current sensor and control switching of the switchable load in which the control circuit is configured to switch the switchable load off and receive current information from the current sensor representing a first current level; switch the switchable load on and receive current information from the current sensor representing a second current level; and detect an error if the difference between the first and second current levels is outside a permitted range.

In some configurations, a respiratory or surgical humidifier can comprise a power flow controller configured to supply power via a supply path to respective output terminals; a switchable load electrically connected across the output terminals; a current sensor that monitors current supplied via the supply path to develop current information; a control circuit configured to receive the current information from the current sensor, control switching of the power flow controller to supply power via the output terminals and control switching of the switchable load with the control circuit configured to: switch the power flow controller on whilst the switchable load is switched off and receive current information from the current sensor representing a first current level; switch the power flow controller on whilst the switchable load is switched on and receive current information from the current sensor representing a second current level; detect an error if the second current level is outside a permitted range; and detect an error if the difference between the first and second current levels is outside a permitted range.

In some configurations, a respiratory or surgical humidifier can comprise: a power flow controller configured to supply power via a supply path to respective output terminals; a switchable load electrically connected across the output terminals; a current sensor that monitors current supplied via the supply path to develop current information; a control circuit configured to receive the current information from the current sensor, control switching of the power flow controller to supply power via the output terminals, and control switching of the switchable load with the control circuit configured to: switch the power flow controller on whilst the switchable load is switched on and receive current information from the current sensor representing a test current level; and detect an error if the test current level is outside a permitted range.

In some configurations, a respiratory or surgical humidifier can comprise a power flow controller configured to control power supplied via a supply path to respective output terminals; a switchable load electrically connected across the output terminals; and a control circuit configured to control the switchable load whilst the power flow controller supplies power to the output terminals to perform in use monitoring of the respiratory or surgical humidifier.

In some configurations a respiratory or surgical humidifier can include a housing configured to receive a humidifier chamber; a heater plate configured to transfer heat to a humidifier chamber when received by the housing; a heater element configured to heat the heater plate; and a power controller configured to control a level of power supplied to the heater element.

In some configurations, a method of monitoring the operation of a respiratory or surgical humidifier having output terminals for supplying power to a heater element of a gas supply tube can comprise temporarily connecting a dummy load across the output terminals whilst power is supplied to the heater element and evaluating one or more power supply attributes to monitor correct operation of the respiratory humidifier.

In some configurations, an error in the operation of the respiratory or surgical humidifier can be detected if a current supplied via the output terminals is below a threshold value.

In some configurations a first current supplied via the output terminals can be measured when the dummy load is not connected across the output terminals and a second current supplied via the output terminals can be measured when the dummy load is electrically connected across the output terminals and an error in the operation of the respiratory or surgical humidifier can be detected if the difference between the first and second currents is outside a permitted range.

In some configurations a respiratory or surgical humidifier includes a transient current detector in the power supply path configured to detect positive or negative transient voltages across an inductor in the supply path.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below. For example, component values and operating parameters are examples only and are not limiting.

Example Respiratory or Surgical Humidifier

The present disclosure provides examples of a respiratory humidifier configured to supply humidified and/or heated gas to a patient or user in multiple modes. The modes for the respiratory humidifier can include at least an invasive mode (for example, for patients with a bypassed airway) and a noninvasive mode (for example, for patients or users with breathing masks). Each mode can have individualized humidity output, which can be expressed as dew point output set points. For example, a user can select a set point appropriate for the current mode of operation. The noninvasive mode can have selectable dew point set points of, for example, 31 degrees Celsius, 29 degrees Celsius, 27 degrees Celsius, or others. The invasive mode can have a dew point set point of 37 degrees Celsius or others. Alternatively, the dew point set points may be continuously variable between upper and lower limits. Some respiratory humidifier systems disclosed herein can also include a high flow, unsealed mode or any other modes known to those of skill in the art. The disclosed circuits and methods may be similarly applied in a surgical humidifier which may be used, for example, in laparoscopic surgery.

Figures 1A, 1B, 1D:
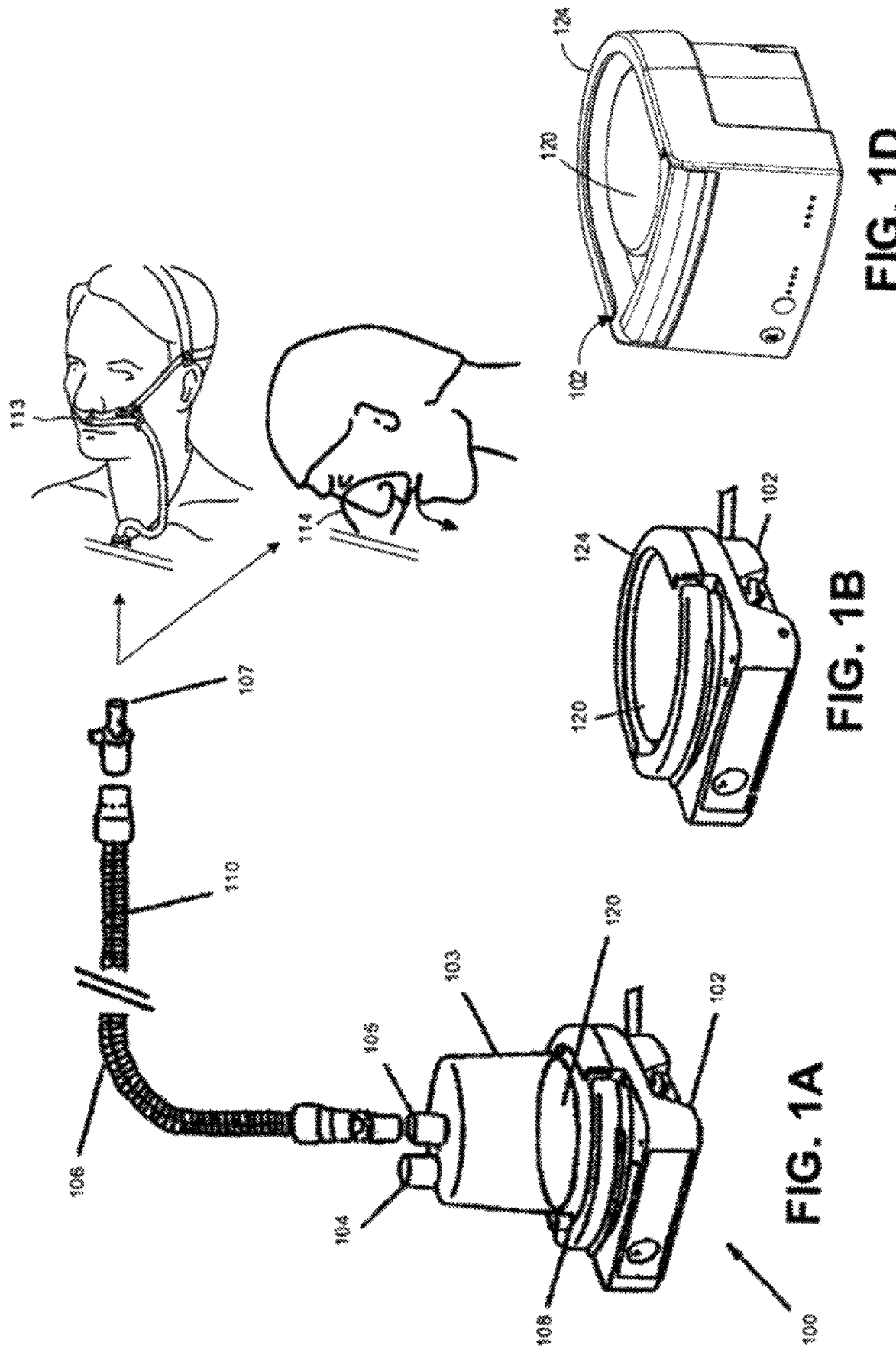
FIG. 1A illustrates schematically an example respiratory humidifier system.
FIG. 1B illustrates schematically an example heater base unit of the respiratory humidifier system of FIG. 1A.
FIG. 1D illustrates schematically an example heater base unit of the respiratory humidifier system of FIG. 1C.
Figures 1C, 1E:
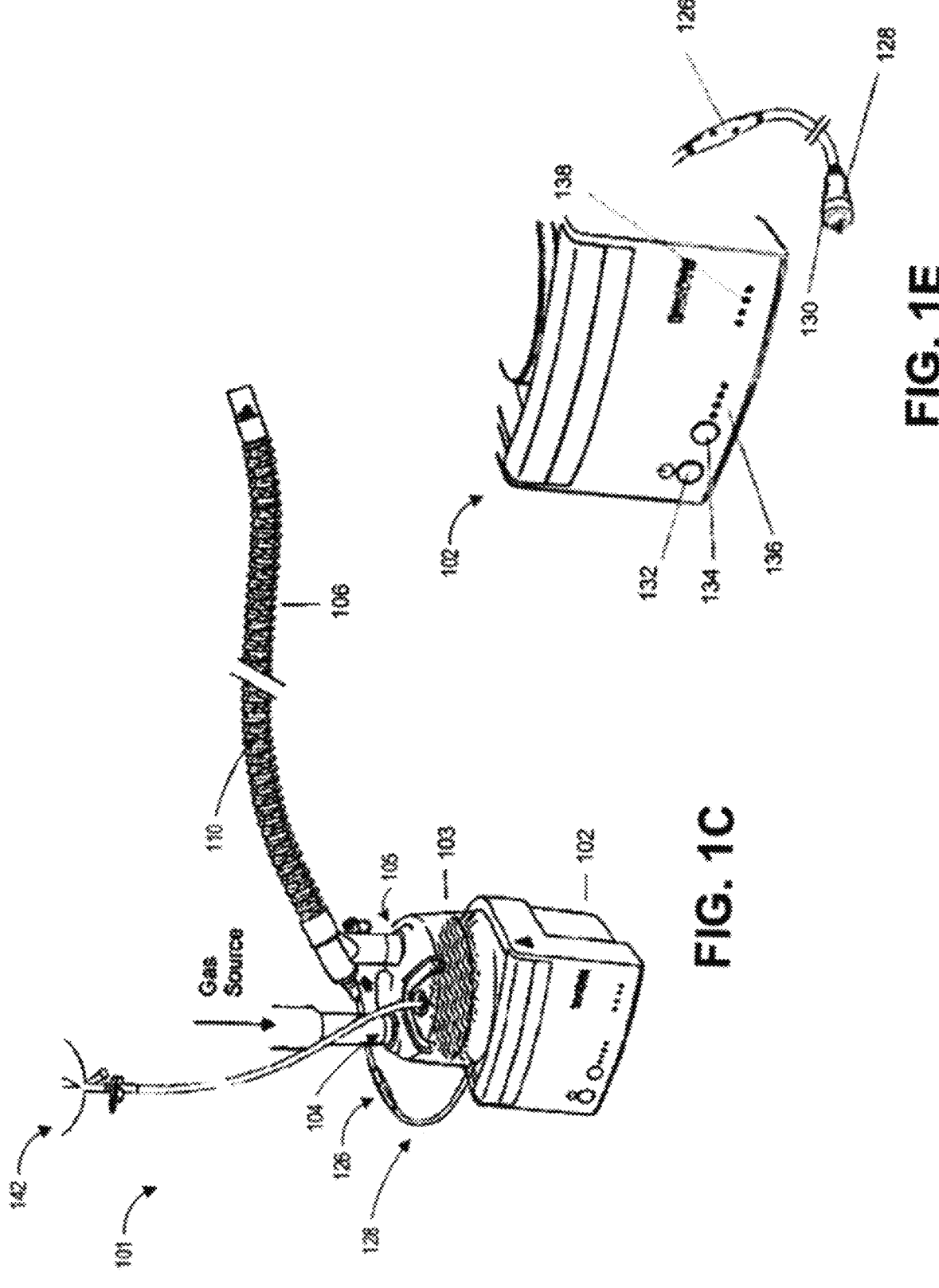
FIG. 1C illustrates schematically an example respiratory humidifier system.
FIG. 1E illustrates schematically a partial view of the heater base unit and an example breathing circuit tube heating element adapter of FIG. 1C.

Referring to FIGS. 1A and 1C, an example respiratory humidifying system 100, 101 can include a heater base unit 102 having a heater plate 120 (see FIGS. 1B and 1D). The heater plate 120 can include one or more heating element(s). The heater base unit 102 can have a housing and a controller (for example, a microprocessor) contained within the housing for controlling the supply of energy to the heating element(s) of the heater plate 120.

The humidifier heater plate 120 can have a temperature sensor (for example, a temperature transducer, thermistor, or other types of temperature sensor). Multiple different temperature sensors may also be used. The temperature sensor can measure a temperature of the heater plate 120. The temperature sensor can be in electrical communication with the controller in the heater base unit 102 so that the controller can monitor the temperature of the heater plate 120.

The humidifier chamber 103 can be removably received and retained on the heater base unit 102, such that the humidifier chamber base is positioned in contact with the heater plate 120 in the heater base unit 102. Referring to FIGS. 1B and 1D, which illustrate examples of the heater base unit 102 of FIGS. 1A and 1C respectively, the humidifying base 102 can have a collar 124 for engaging with a flange on the humidifier chamber 103, such as shown in FIGS. 1A and 1C. The collar 124 defines a lip that engages a flange of the humidifier chamber 103 to retain the humidifier chamber 103 in an operative position on the heater base 102. The humidifier chamber 103 can include a thermally conductive base. When engaged with the heater base unit 102, the conductive base of the humidifier chamber 103 can be in contact with the heater plate 120, such as an upper surface of the heater plate 120. Water inside the chamber 103 is heated when a power signal is sent to the heating element to energize the heating element. The chamber 103 can also be connected to a water source 142 (FIG. 1C), which can add water to the chamber 103 when the water is low or completely out in the chamber 103. Adding of water can be manually performed, such as upon a warning from the system 101 that there may be a low water or water-out condition, or automatically performed, such as using a float valve connected to a water supply.

With continued reference to FIGS. 1A and 1C, the gases to be humidified can include one or more of air, oxygen, anesthetic, other auxiliary gases, or any mixture of gases. The gases can be supplied to the humidifier chamber 103 through a gas inlet 104, which can be connected to a gas source, such as a ventilator, in the case of CPAP therapy a CPAP blower, or a remote source. For high flow therapy, a blower or further alternatively a wall source with a flow and/or pressure regulator can supply the gases. The humidifier chamber 103 also includes a gases outlet 105, which can connect to a breathing circuit 106. The breathing circuit 106 can convey humidified and heated gases to a patient or user. As shown in FIG. 1A, a patient end 107 of the breathing circuit 106 can connect to a patient interface, such as a nasal cannula 113 or a nasal mask 114. The breathing circuit 106 can also connect to other types of patient or user interfaces, such as a full-face mask, total-face mask, nasal pillows mask, endotracheal tube, or others. The breathing circuit 106 of FIG. 1C can similarly be connected to any suitable patient interface. The breathing circuit 106 may include a gas supply tube with or without a tube heating element. The respiratory humidifying system 100, 101 may be configured for use with both heated and unheated gas supply tubes or breathing circuits.

A tube heating element 110 (such as one or more heater wires embedded in the gas supply tube wall, contained within the gas supply tube, or wrapped around the outside of the gas supply tube) can be provided in the breathing circuit 106. The tube heating element 110 can help prevent condensation of the humidified gases within the breathing circuit 106. The tube heating element 110 can also optionally be in electrical communication with the controller in the heater base unit 102. As shown in FIGS. 1C and 1E, a breathing circuit tube heating element adaptor cable 128 can have two connectors at two ends of the cable 128 for coupling the tube heating element 110 to the heater base unit 102 (such as to the controller of the heater base unit 102).

Alternatively, the tube heating element adapter cable may be permanently electrically connected to a tube heating element supply circuit of the heater base unit 102, for example by soldering. The tube heating element adaptor cable 128 can facilitate an easy connection between the tube heating element 110 and the heater base unit 102. The tube heating element 110 is controlled by the controller, including the controlling of power to the tube heating element 110. The tube heating element 110 in the breathing circuit 106 reduces condensation and ensures the temperature and/or humidity of gases is maintained in a predetermined range. The tube heating element adaptor cable 128 can also include an ambient temperature sensor 126, which can allow the system 101 to adjust the tube heating element 110 power and/or heater plate power to compensate for ambient temperatures or changes in the ambient temperature. The ambient temperature sensor can alternatively be located anywhere that is exposed to the ambient air. A tube heating element indicator 130 can be embedded into the connector that couples to the heater base unit 102. The tube heating element indicator 130 can be illuminated when a properly functioning tube heating element 110 is connected to the heater base unit 102, and the system 101 can heat the gas inside the breathing circuit 106 via the tube heating element 110 to minimize condensate in addition to heating the gas passing through the humidifier chamber 103 via the heater plate 120. If the tube heating element 110 is malfunctioning or not connected, the tube heating element indicator 130 is not illuminated (or is flashing), and the system 101 may heat the gas only by heating the water in the chamber 103 via the heater plate 120. Alternatively, the tube heating element indicator 130 may be illuminated when there is a fault or a disconnection of the adaptor cable 128 from the tube heating element 110. The illuminated indicator 130 can act as a visual message or a visual warning. The indicator 130 may not be illuminated if the tube heating element 110 is functioning correctly.

The controller of the respiratory humidifier system 100, 101 can control at least the heater plate 120, and preferably or optionally also the tube heating element 110, without additional sensors (for example, in the humidifier chamber, at the chamber outlet, in the breathing circuit, and/or elsewhere in the system). This can be achieved by estimating a heater plate operating point required to deliver a required humidity. For a given respiratory humidifier system, the controller can determine an appropriate level of power to apply to the heater plate 120. Applying power to the heater 120 can generate humidity and heat the gases. The heater plate power and temperature can be controlled to generate a predetermined amount of humidity. Additionally, the parameters can also optionally be used by the controller to provide a more appropriate level of energization to the tube heating element 110. As shown in FIGS. 1C and 1E, the system 101 can also include the ambient temperature sensor 126. The ambient temperature sensor can be located anywhere that is exposed to the ambient air. For example, the system 101 can include the ambient temperature sensor 126 on the tube heating element adaptor cable 128.

As shown in FIG. 1E, a front panel of the heater base unit 102 can include a plurality of user controls and indicators, such as a power button 132, a humidity setting push button 134, and a plurality of (such as three, four, five or more) humidity settings indicators 136 (which can include LED lights) next to the humidity setting push button 134. The locations, shapes, and sizes of the user controls and indicators are not limiting. There can be four levels of humidity settings available which are indicated by the four humidity setting indicators 136. The four humidity settings may correspond to different types of therapies provided to a patient. For example, the highest amount of humidity can be selected when the humidifier is operating in an invasive therapy mode. The lowest amount of humidity may be applied in a low flow oxygen therapy mode. The amount of humidity can be selected based on therapeutic requirements or therapy type, or it may be predefined. Alternatively, the humidifier 100, 101 may include a controller that is configured to automatically select the amount of humidity to be delivered based on a therapy mode, the patient, or the type of therapy being applied to the patient. Optionally, the humidifier 100, 101 may include a display or touch screen that may communicate information to the user. The touch screen may also be configured to receive inputs from the user.

The humidity level can be adjusted by pressing the humidity settings push button 134, which can also be a momentary push button. The front panel can also include a plurality of alarm indicators 138 (which can include LED lights) to indicate the following non-limiting examples of conditions: "water out" condition (including low water and water-out), tube heating element adaptor not connected, audible alarm muted, and a "See Manual" indication used to indicate that a fault has occurred within the system 101.

The system 101 can be suitable for providing respiratory therapy for different purposes, such as for critical care (for example, in the hospital) and home care. The system 101 is suitable for providing invasive, non-invasive and high flow therapies for both adult and pediatric patients.

Figure 2:
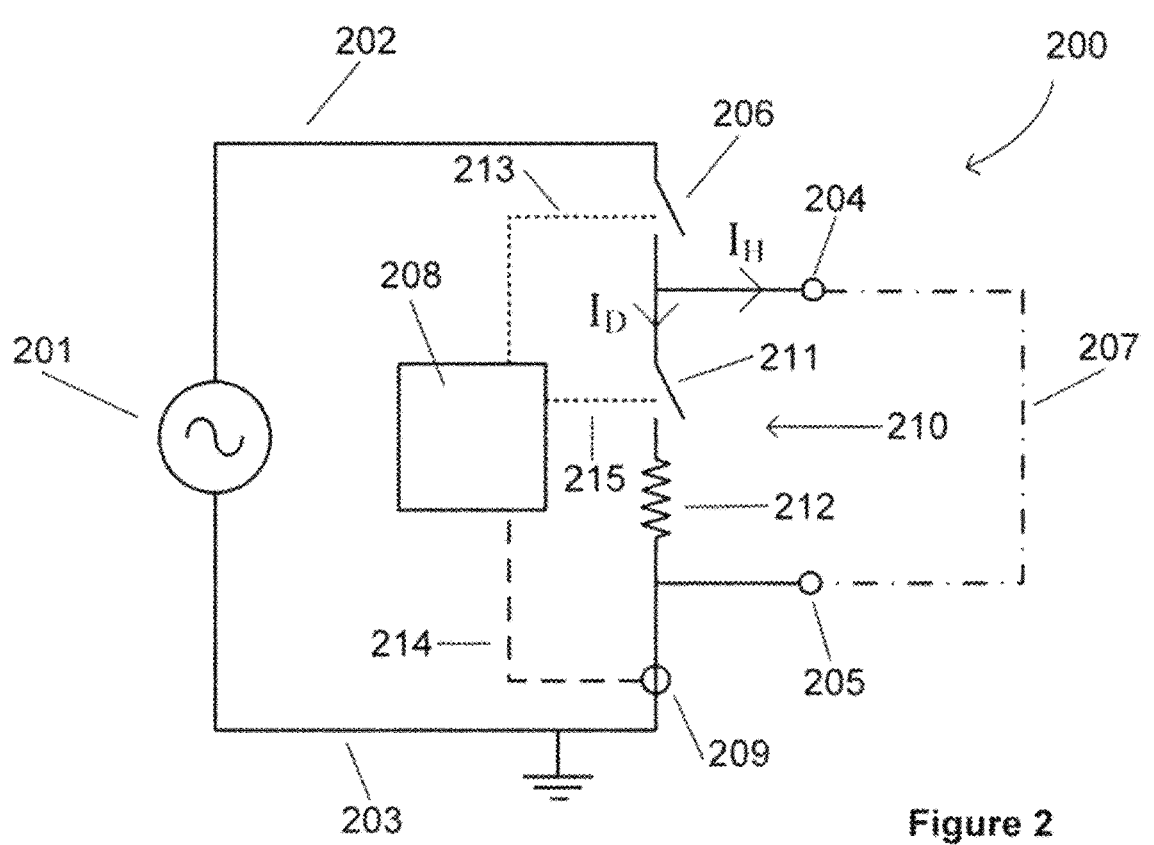
FIG. 2 illustrates an example circuit for monitoring the operation of a respiratory or surgical humidifier.

With reference to FIG. 2, an example tube heating element supply circuit for a respiratory or surgical humidifier can include an electric power source 201 that can supply power via a power supply path (which includes a power flow controller 206 and power supply lines 202 and 203) to output terminals 204 and 205. Power source 201 could be an AC or DC power supply but in this example is an AC power supply (including a transformer that reduces the supply voltage from mains voltage to about 22 Volts). A tube heating element 207 can be connected to output terminals 204 and 205 when the respiratory or surgical humidifier is providing therapy to heat gases within a gas supply tube. The tube heating element 207 can be in the form of one or more heater wires embedded in a gas supply tube wall, contained within the gas supply tube, wrapped around the outside of the gas supply tube, or otherwise.

In this example, power flow controller 206 can be a controllable switch, such as a semiconductor switch, controlled by a control circuit 208 via control line 213. Power flow controller 206 could alternatively supply a number of different power levels or continuously vary the level of power supplied via the supply path. Control circuit 208 can include a microprocessor. Control circuit 208 can control the switching of flow controller 206 when a tube heating element is connected to ensure that a required amount of heating is provided to a gas within a gas supply tube. The tube heating element supply circuit can include a current sensor 209 for monitoring the current flowing in the supply path and providing attribute information in the form of the current level via data line 214 to control circuit 208. The current sensor 209 can be an inductive, Hall effect or shunt resistor-based sensor.

The tube heating element supply circuit can also include a switchable load 210 electrically connected across the output terminals 204 and 205. Switchable load 210 can include a controllable switch 211 in series with a "dummy" load 212. The controllable switch can be a semiconductor switch controlled by control circuit 208 via control line 215.

The load 212 can be a resistance but can also be another form of impedance or composite impedance.

The control circuit 208 can be configured to control the switchable load 210 to test the operation of the respiratory or surgical humidifier either when no tube heating element 207 is connected across output terminals 204 and 205 or whilst power is supplied to the output terminals with a tube heating element 207 connected across output terminals 204 and 205 during therapy.

The control circuit 208 can also be configured to control the power flow controller 206 and the switchable load 210 to operate in different state combinations and monitor the operation of the respiratory or surgical humidifier. This monitoring may be based on the attribute information received from the current sensor 209 for different switch states of the switchable load 210 and power flow controller 206.

In one example the tube heating element supply circuit 200 of FIG. 2 may be used in a fault checking method (where a tube heating element 207 is connected across terminals 204 and 205) where the following steps can be performed:

i. Control circuit 208 controls power flow controller 206 to switch on (if it is open at the start of the fault check) whilst switch 211 of switchable load 210 is switched off.

ii. Control circuit 208 receives attribute information in the form of a current level measurement from current sensor 209. In this case, where the power flow controller 206 and switch 211 are working as intended, a first current level ($I_H$) flowing through tube heating element 207 is measured.

iii. Control circuit 208 controls switch 211 of controllable load 210 to turn on.

iv. Control circuit 208 receives attribute information in the form of a second current level measurement from current sensor 209. In this case, where the power flow controller 206 and switch 211 are working as intended, the second current level measured is the sum of $I_H$ flowing through tube heating element 207 and the current $I_D$ flowing through the dummy load 212 (in this case a resistor).

v. Control circuit 208 (in this case including a microprocessor) determines the difference between the currents (referred to as "$\Delta I$") being the second current level measured in step iv. minus the first current level measured in step ii.

vi. Control circuit 208 can determine whether there is a fault (potentially a fault in current sensor 209 or alternatively a fault in dummy load 212, dummy load switch 211 or power flow controller 206) by checking whether the difference in current ($\Delta I$) is within a permitted current range.

vii. Control circuit 208 can determine whether a tube heating element is present or whether there is a fault (potentially a fault in the power flow controller 206 or tube heating element 207) by checking whether the first current level measured in step ii., ($I_H$), is within a permitted range.

viii. Control circuit 208 can also determine that there is a fault in power flow controller 206 if the current measured by current sensor 209 is above a low current threshold level (at or near zero) when power flow controller 206 is switched off and dummy load switch 211 is switched on. With dummy switch 211 switched on such a fault may be detected whether a tube heating element is in circuit or not. Alternatively, where for example a heater wire is permanently connected, just the current $I_H$ may be measured when power flow controller 206 is switched off and dummy load switch 211 is switched off. If the current is above a low current threshold level, for example 0.1 A, it may be determined that there is a fault in power flow controller 206.

It will be appreciated that not all of above steps need be carried out and that in some implementations only one or a selection of steps may be implemented. It will also be appreciated that the selected steps may be carried out in a different sequence.

By using the difference between currents in step vi. the fault checking method above may be performed whether a tube heating element is present or not, whether a tube heating element (if present) is functioning correctly or not, and whether a connected tube heating element is being used to provide therapy or not, as will be explained below. As the current difference may be expressed as:

$$\Delta I = (I_D + I_H) - I_H$$

Therefore:

$$\Delta I = I_D$$

Thus, the current $\Delta I$ will be equal to ID irrespective of whether a heater wire is present or absent. This is because the current flowing through the heater wire is cancelled out in all cases.

Knowing that the test in step vi. isolates the current component ID flowing through the controllable load 210, the expected current sensed by current sensor 209 will be the supply voltage divided by the resistance of load 212. The permitted current range in step vi. may be the expected current plus or minus a permitted margin of error. For example, assuming no fault is present, with a 22V supply voltage and a 470Ω resistance, the permitted range may be 22/470+/−20% (or some other acceptable error range). The test in step vi. may therefore test whether the control circuit is operating outside a permitted range (potentially due to a fault in the current sensor or a component in the supply path).

In step vii. the current IH flowing through the tube heating element 207 may be monitored to determine whether a tube heating element 207 is present or not and, if present, if it is operating within an acceptable range (assuming no other faults have been identified in step vi.). The permitted current range may be the expected current plus or minus a permitted margin of error (for example +/−20%). In this case the expected current may be IH=V/RHeating_Element_207 where V is the supply voltage across the output terminals. Alternatively, the expected current could be based on the current measured at step iv. In this case the expected current would be ID+IH=V/RResistor_212+V/RHeating_Element_207 and this may be tested against the current measured in step iv. For example, with a 22V supply voltage, a 470Ω resistance 212, and a 24Ω heater wire, the permitted range may be (22/470+22/24)+/−20% (or some other acceptable error range). The test can alternatively simply be whether the expected current is below a lower threshold (i.e. ID+IH<(V/RResistor_212+V/RHeating_Element_207)*x %, where x provides a margin of error), or, using the values above, where the expected current is less than 0.8*(22/470+ 22/24).

Where no fault is detected in step vi. and the current IH is zero or negligible control circuit 208 may determine that a tube heating element is not present or not operating correctly. In some configurations a tube heating element may only be required where high levels of humidification are required. In such configurations if a user attempts to use a high humidification level where a tube heating element is not present or not working correctly control circuit 208 may provide a visual alert via indicators 136 and/or provide an audible alert and/or communicate an alert condition to a remote device and/or inhibit certain functionality (depending upon the nature of the fault detected). For lower levels of humidification, therapy may be provided without the need for the tube heating element to be driven.

Control circuit 208 can run a fault check when the humidifier starts up and then intermittently during operation (e.g., every 10 minutes or every 2 hours). Each fault check occurrence has a negligible effect on the operation of the humidifier, due to the independence of the controllable load 210 from the tube heating element current path.

Figure 3:
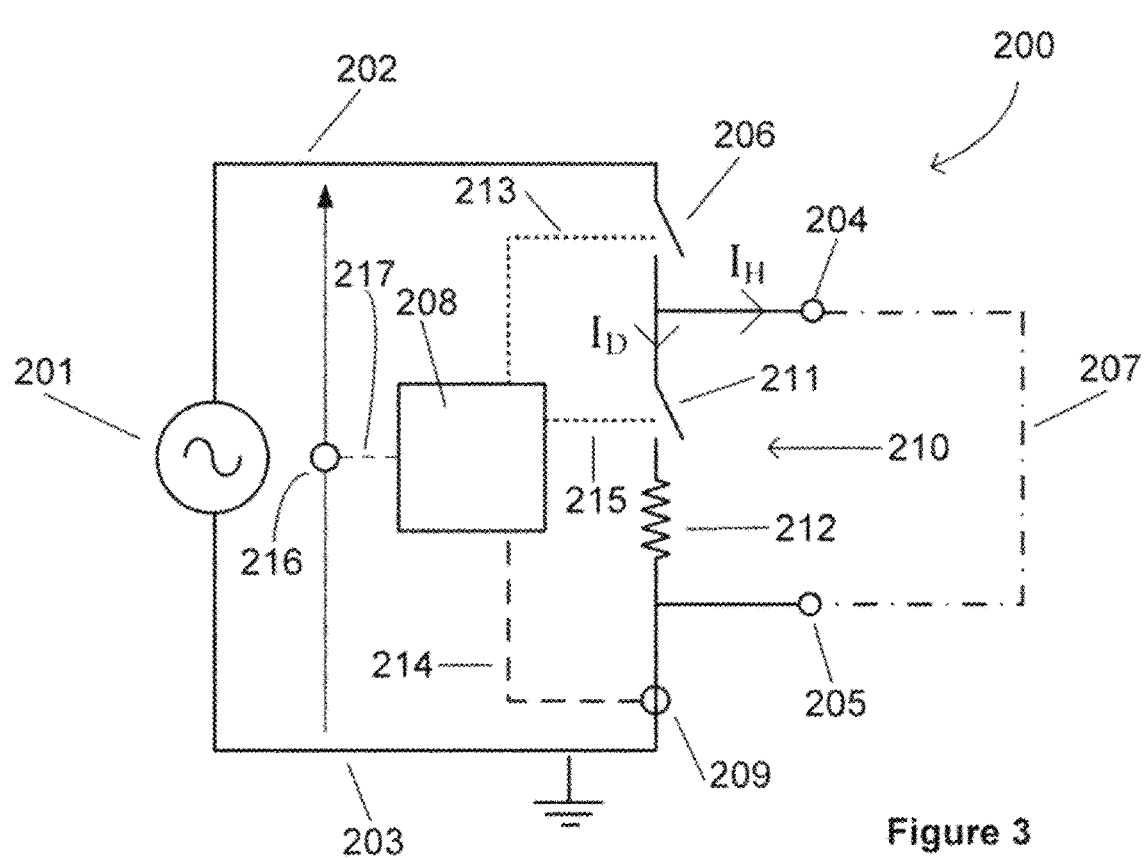
FIG. 3 illustrates a modified example circuit for monitoring the operation of a respiratory or surgical humidifier.

With reference to FIG. 3, an example tube heating element supply circuit for a respiratory or surgical humidifier can also include a voltage sensor 216 for sensing the voltage across the voltage source and providing voltage information via a data line 217. The remaining circuit components are as in FIG. 2 and so the same numerals have been used. Operation may be the same as for FIG. 2 except that instead of assuming a constant voltage supply the actual supply voltage may be used by control circuit 208. This circuit may be appropriate where there is substantial variation of the supply voltage. This circuit also allows the identification of a fault due to the supply voltage not being within a required range.

In one example, the tube heating element supply circuit of FIG. 3 can perform a fault checking method (where a tube heating element 207 is connected across terminals 204 and 205) where the following steps are performed:

i. Control circuit 208 controls power flow controller 206 to switch it on (if it is open at the start of the fault check) whilst switch 211 of switchable load 210 is switched off.

ii. Control circuit 208 receives attribute information in the form of a first current level measurement from current sensor 209. In this case the current $I_H$ flowing through tube heating element 207 is measured. Control circuit 208 also receives attribute information in the form of a voltage level measurement from voltage sensor 216. A resistance can then be calculated using Ohm's law representing the resistance $R_H$ of the tube heating element 207.

iii. Control circuit 208 controls switch 211 of controllable load 210 to turn on.

iv. Control circuit 208 receives attribute information in the form of a second current level measurement from current sensor 209. In this case the sum of current $I_H$ flowing through tube heating element 207 and the current $I_D$ flowing through resistor 212 is measured $(I_D + I_H)$. Control circuit 208 also receives attribute information in the form of a voltage level $(V_{iv})$ measurement from voltage sensor 216.

v. Control circuit 208 (in this case including a microprocessor) determines an expected second current level $I_{exp}$ according to the formula:

$$I_{exp} = \left( \frac{V_{iv}}{R_H} + \frac{V_{iv}}{R} \right)$$

where R is the known resistance 212.

vi. Control circuit 208 determines the difference between the current levels ($\varepsilon$I) being the expected second current level $I_{exp}$ minus the first current level ($I_H$) measured in step ii.

vii. Control circuit 208 determines whether there is a fault in current sensor 209 (or another component in the supply path) by checking whether the difference in current ($\varepsilon$I) is within a permitted current range.

viii. Control circuit 208 can also determine whether there is a fault in the power flow controller 206 by checking whether the second current level measured in step iv. ($I_D+I_H$) is within a permitted range. Control circuit 208 can determine whether a tube heating element is present or whether there is a fault (potentially a fault in the power flow controller 206 or tube heating element 207) by checking whether the first current level ($I_H$) measured in step ii. is within a permitted variance from an expected first current level $V_{iv}/R_H$.

ix. Control circuit 208 can also determine whether there is a fault in power flow controller 206 by checking whether the second current level ($I_D+I_H$) is above a low current threshold level (at or near zero) when power flow controller 206 is switched off and dummy load switch 211 is switched on. Alternatively, where for example a heater wire is permanently connected, just the first current level ($I_H$) may be measured when power flow controller 206 is switched off and dummy load switch 211 is switched off. If the current is above a low current threshold level, for example 0.1 A, it may be determined that there is a fault in power flow controller 206.

Should it be determined that a fault condition exists, control circuit 208 can turn off the power flow controller 206 and/or provide a visual alert via indicators 136 and/or provide an audible alert and/or communicate an alert condition to a remote device and/or inhibit certain functionality (depending upon the nature of the fault detected).

Figure 4:
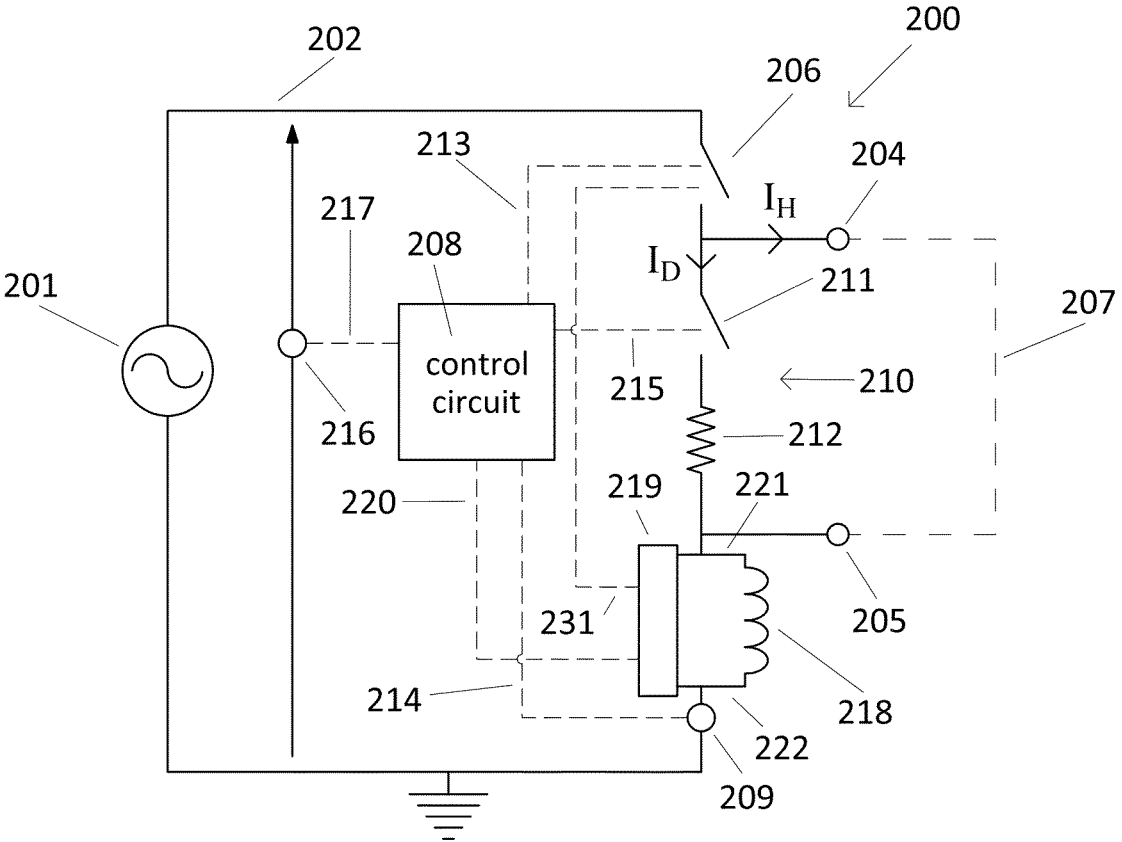
FIG. 4 illustrates an example circuit (including a transient current detector) for monitoring the operation of a respiratory or surgical humidifier.

With reference to FIG. 4, an example tube heating element supply circuit for a respiratory or surgical humidifier can also include a transient current detector capable of detecting transient currents outside of a permitted range. Transient currents in the form of short-lived, aperiodic spikes in the supply current could potentially arise in the case of a heater wire breakage and could potentially cause a gas supply tube to have a high surface temperature, melt or ignite from sparking. These situations can also occur from EMI and/or mains surge. To protect against these situations, a transient current detector can cause power supply to a tube heating element to be stopped where transient currents outside a permitted range are detected.

In the circuit shown in FIG. 4, like elements to those shown in FIGS. 2 and 3 are given like numbers. As shown in FIG. 4, an inductor 218 may be included in the power supply path with sense lines 221 and 222 connected to a transient current detection circuit 219. When transient current detection circuit 219 detects a transient current outside of a permitted range it can send a transient current detection signal or a feedback signal via signal line 220 to control circuit 208. In response, control circuit 208 can turn power flow controller 206 off to terminate power supply to the tube heating element. Additionally and/or alternatively the transient current detection circuit 219 can turn power flow controller 206 off directly via signal line 231 to terminate power supply to the tube heating element. Additionally and/or alternatively control circuit 208 can turn off other components, such as the heater plate, or generate an alarm when transient current detection circuit 219 detects a transient current outside of a permitted range Although FIG. 4 illustrates a circuit further comprising the switchable load 210 described above, it will be appreciated that the disclosed transient current detector may alternatively be used independently of the disclosed fault detection methods and circuits.

Figure 5:
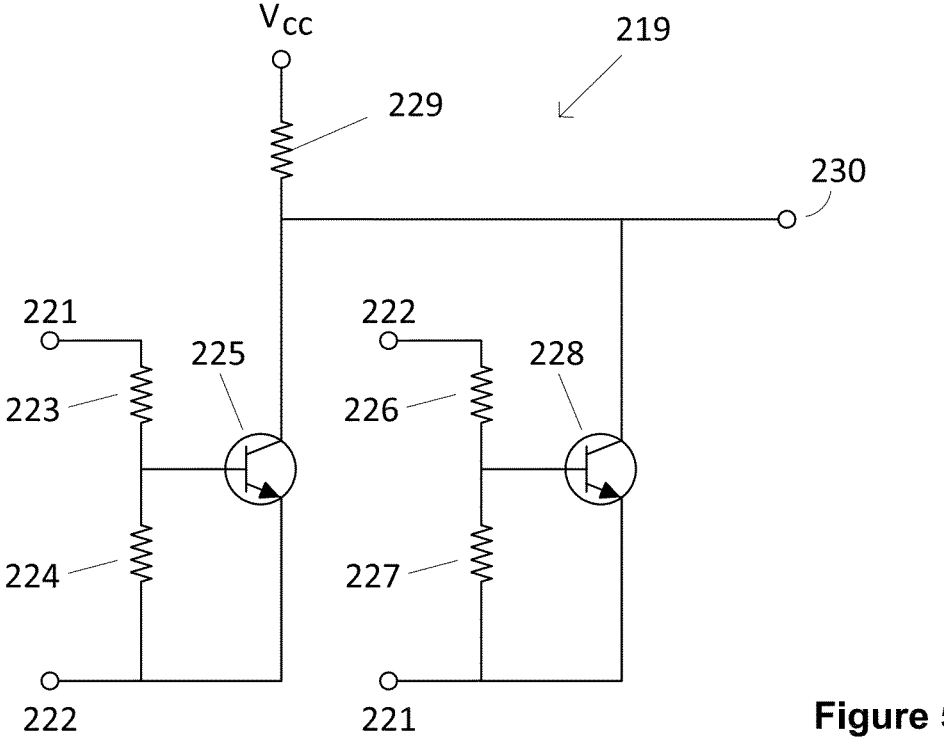
FIG. 5 illustrates an example circuit for the transient current detector circuit shown in FIG. 3.
Figure 6:
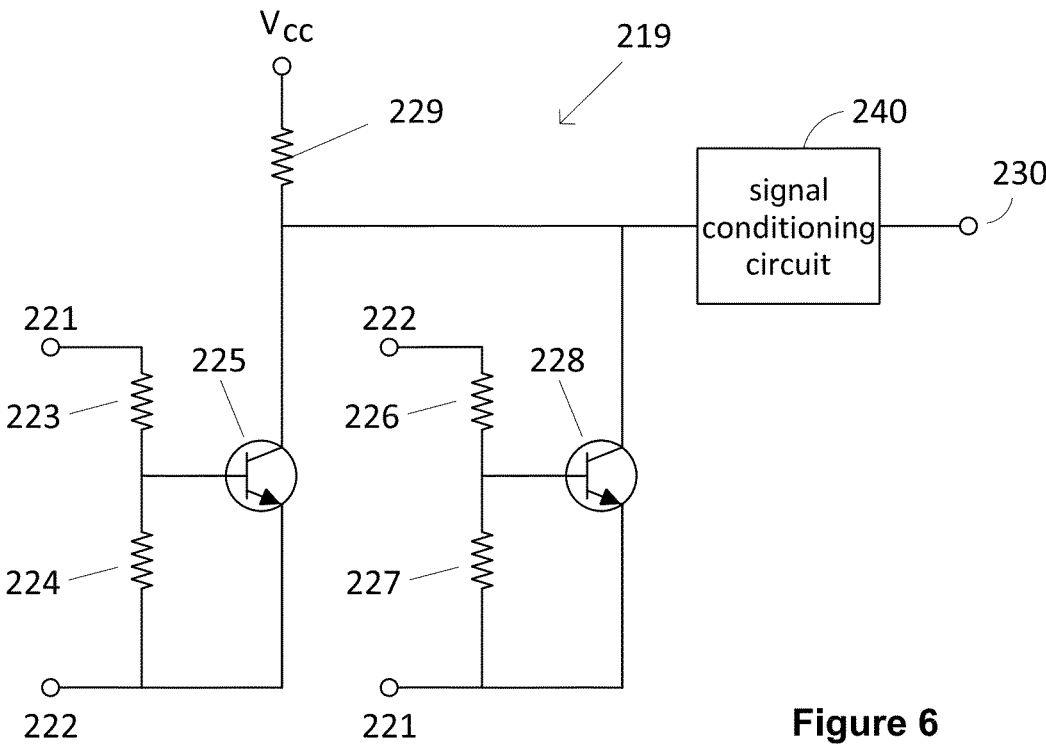
FIG. 6 illustrates a modified form of the transient current detector circuit shown in FIG. 5.

FIG. 5 shows a simple transient current detection circuit 219 that can be used to detect transient currents. A first transistor detection circuit, including transistor 225 and biasing resistors 223 and 224, is connected to sense lines 221 and 222 and switches on when a difference in sense line voltages (V221-V222) is above a permitted level. A second transistor detection circuit, including transistor 228 and biasing resistors 226 and 227, is also connected to sense lines 221 and 222 and switches on when a difference in sense line voltages (V222-V221) is above a permitted level. Biasing resistor 229 holds transient current detection output signal line 230 high when both transistor 225 and 228 are switched off (high resistance). Output signal line 230 is connected to power flow controller 206 by line 220. When either transistor 225 or 228 switches on, transient current detection output signal line 230 is pulled down and in response control circuit 208 can turn off power flow controller 206. FIG. 6 shows a modified transient current detection circuit 219 which is the same as FIG. 5 except that a signal conditioning circuit 240 is provided prior to output signal line 230. It may be desirable for output signal line 230 to be held or extended in a pulled down state for a period of time rather than just during the period that transient currents are detected. The signal conditioning circuit 240 can be a monostable multivibrator with a pre-defined delay or some other suitable circuit.

By connecting sense lines 221 and 222 with opposite polarity to the transistor detection circuits a window detector may be provided to detect positive and negative transient currents using a simple circuit employing only two transistors without using a bridge rectifier or a negative power supply.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in non-volatile memory, such as an erasable programmable read-only memory (EPROM). It will be further appreciated that hardware modules may comprise connected logic units, such as gates, flip-flops and/or application specific integrated circuits, and/or may comprise programmable units, such as programmable gate arrays and/or processors. The modules described herein can be implemented as software modules, but also may be represented in hardware and/or firmware. Moreover, although in some embodiments a module may be separately compiled, in other embodiments a module may represent a subset of instructions of a separately compiled program and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A respiratory or surgical humidifier configured to connect to a gas supply tube, the respiratory or surgical humidifier comprising:
    power supply lines configured to supply power via a supply path to respective output terminals, the output terminals configured such that a heating element of a gas supply tube can be connected across the output terminals;
    a switchable load within the respiratory or surgical humidifier, the switchable load electrically connected across the output terminals;
    a control circuit configured to control switching of the switchable load; and
    a sensor that monitors at least one attribute of power supplied via the supply path and provides attribute information to the control circuit, wherein the control circuit is configured to control the switchable load to operate in different states and detect a fault of the respiratory or surgical humidifier based on the attribute information for the different states.

2. The respiratory or surgical humidifier of claim 1, wherein the control circuit is configured to control the switchable load to test the respiratory or surgical humidifier whilst power is supplied to the heating element electrically connected across the output terminals.

3. The respiratory or surgical humidifier of claim 1, wherein the switchable load comprises one or more of a controllable switch, an impedance, a reactive impedance, a resistor, or a semiconductor switch.

4. The respiratory or surgical humidifier of claim 1, further comprising a voltage sensor across the power supply lines and wherein the attribute information comprises the voltage across the power supply lines.

5. The respiratory or surgical humidifier of claim 1, wherein the sensor comprises one or more of an inductive sensor, a Hall effect sensor, or a shunt resistance-based sensor; and wherein the attribute information comprises a current flowing in the supply path.

6. A respiratory or surgical humidification system comprising the respiratory or surgical humidifier of claim 1, the system further comprising a gases supply tube, wherein the heating element of the gases supply tube is electrically connected across the output terminals, in parallel with the switchable load.

7. The respiratory or surgical humidifier of claim 1, wherein the sensor comprises a current sensor.

8. The respiratory or surgical humidifier of claim 1, the control circuit is configured to receive first attribute information from the sensor representing a first attribute level while the switchable load is switched off, and receive second attribute information from the sensor representing a second attribute level while the switchable load is switched on.

9. The respiratory or surgical humidifier of claim 8, wherein the control circuit is configured to receive current information from a current sensor and wherein the first attribute information is current information from the current sensor representing a first current level flowing in the supply path whilst the switchable load is switched off.

10. The respiratory or surgical humidifier of claim 9, wherein the control circuit is configured to detect an absence of the heating element or an error if the first current level is outside a permitted range.

11. The respiratory or surgical humidifier of claim 10, wherein the control circuit is configured to receive current information from the current sensor and wherein the second attribute information is current information from the current sensor representing a second current level flowing in the supply path whilst the switchable load is switched on.

12. The respiratory or surgical humidifier of claim 10, wherein the permitted current range for the difference between a first and second current levels is determined on a basis of a voltage level across the output terminals, and a switchable load.

13. The respiratory or surgical humidifier of claim 8, wherein the control circuit is configured to detect a fault of the respiratory or surgical humidifier if a comparison between the first and second attribute levels is outside a permitted range.

14. The respiratory or surgical humidifier of claim 13, wherein the comparison comprises a difference between the first and second attribute levels.

15. A method of monitoring an operation of a respiratory or surgical humidifier having a power supply path and output terminals for supplying power to a tube heating element of a humidifier supply tube, the method comprising:
    temporarily connecting a dummy load across the output terminals while power is supplied to the tube heating element;
    evaluating a first power supply attribute when the dummy load is connected across the output terminals and a second power supply attribute when the dummy load is not connected across the output terminals;
    determining a difference between the first and second power supply attributes; and
    detecting a fault of the respiratory humidifier if the difference between the first and second power supply attributes is outside a permitted range.

16. The method of claim 15, wherein the first power supply attribute is a first current flowing in the power supply path when the dummy load is electrically connected across the output terminals and the second power supply attribute is a second current flowing in the power supply path when the dummy load is not electrically connected across the output terminals.

17. The method of claim 15, further comprising terminating power to the tube heating element if the fault is detected.

* * * * *